United States Patent
Simon

(10) Patent No.: US 7,794,721 B2
(45) Date of Patent: *Sep. 14, 2010

(54) SYNTHESIS OF HUMAN SECRETORY IGM AND THE TREATMENT OF CLOSTRIDIUM DIFFICILE ASSOCIATED DISEASES HEREWITH

(76) Inventor: Michael R. Simon, 1925 Scottwood, Ann Arbor, MI (US) 48104

( * ) Notice: Subject to any disclaimer, the term of this patent is extended or adjusted under 35 U.S.C. 154(b) by 0 days.

This patent is subject to a terminal disclaimer.

(21) Appl. No.: 11/851,606

(22) Filed: Sep. 7, 2007

(65) Prior Publication Data

US 2008/0145370 A1    Jun. 19, 2008

Related U.S. Application Data

(63) Continuation-in-part of application No. 11/839,781, filed on Aug. 16, 2007, now Pat. No. 7,597,891.

(51) Int. Cl.
*A61K 39/00* (2006.01)
*A61K 39/395* (2006.01)
*A61K 39/02* (2006.01)

(52) U.S. Cl. .......... 424/178.1; 424/9.1; 424/9.2; 424/130.1; 424/139.1; 424/141.1; 424/150.1; 424/234.1; 424/236.1; 424/239.1

(58) Field of Classification Search .......... 424/9.1, 424/9.2, 130.1, 139.1, 141.1, 150.1, 178.1, 424/234.1, 236.1, 239.1
See application file for complete search history.

(56) References Cited

U.S. PATENT DOCUMENTS

| | | | |
|---|---|---|---|
| 5,190,752 A | 3/1993 | Moller et al. | |
| 5,773,000 A * | 6/1998 | Bostwick et al. | 424/167.1 |
| 6,162,904 A | 12/2000 | Mamidi et al. | |
| 6,932,967 B2 * | 8/2005 | Simon | 424/130.1 |
| 6,967,106 B2 * | 11/2005 | Simon | 436/513 |
| 7,186,410 B2 | 3/2007 | Chtourou et al. | |

OTHER PUBLICATIONS

Kelly, C.P. Immune response to Clostridium difficile infection. European Journal of Gastroenterology & Hepatology. vol. 8, No. 11, pp. 1048-1053. 1996.*

Mulligan, M.E., et al. Elevated levels of serum immunoglobulins in asymptomatic carriers of Clostridium difficile. Clinical Infectious Diseases, vol. 16, suppl. 4, pp. S239-S244, 1993.*

Saturno, E.J. et al., "Oral Immunoglobulin Therapy in a Child with Severe Clostridium Difficile Diarrhea", LSU Health Sciences Center, New Orleans, LA.(1),, J Allergy Clin Immunol, Feb. 2006, S284 Abstracts.

Bouvet, J.P. et al., "Secretory Component-Binding Properties of Normal Serum IgM", Scand.J. Immunol. 31, pp. 437-441, 1990, Paris, France.

Prinsloo, E. et al., "In vitro refolding of recombinant human free secretory component using equilibrium gradient dialysis", Protein Expression & Purification 47 (2006) 179-185.

Carayannopoulos, L., et al., "Immunoglobulins Structures and Function", Fundamental Immunology, Third Edition, New York, 1993, pp. 283-314.

Delacroix, D.L. et al., "Selective Transport of Polymeric Immunoglobulin A in Bile", J. Clin. Invest., The American Society for Clinical Investigation, Inc., 0021-9738, vol. 70, Aug. 1982, pp. 230-241.

Delacroix, D.L. et al., "Changes in Size, Subclass, and Metabolic Properties of Serum Immunoglobulin A in Liver Diseases and in Other Diseases with High Serum Immunoglobulin A", J. Clin. Invest., The American Society for Clinical Investigation, Inc., 0021-9738; vol. 71, Feb. 1983, pp. 358-367.

* cited by examiner

*Primary Examiner*—Rodney P. Swartz
(74) *Attorney, Agent, or Firm*—Avery N. Goldstein

(57) ABSTRACT

A composition for treating a subject is provided. The composition includes a pentameric secretory IgM therapeutic. Formulating agents are mixed with the pentameric secretory IgM to yield a dosing form of a capsule, tablet, and a suppository. A process for manufacturing a medicament for the treatment of *C. difficile* associated disease in a human is also provided that the modification of pentameric IgM with secretory component to form a pentameric secretory IgM therapeutic. The pentameric secretory IgM therapeutic is then mixed with formulating agents to create a capsule, tablet, or suppository dosing form. The therapeutic is amenable to enrobement directly through microencapsulation or the dosing form is coated with an enteric coating. A method of *C. difficile* treatment with the therapeutic is also provided that is amenable to supplementation with concurrent or prior antibiotic administration.

21 Claims, No Drawings

SYNTHESIS OF HUMAN SECRETORY IGM AND THE TREATMENT OF CLOSTRIDIUM DIFFICILE ASSOCIATED DISEASES HEREWITH

CROSS REFERENCE TO RELATED APPLICATIONS

This application is a continuation-in-part of U.S. patent application Ser. No. 11/839,781 filed Aug. 16, 2007; which is in-turn a continuation-in-part of U.S. patent application Ser. No. 11/610,154 filed Dec. 13, 2006.

FIELD OF THE INVENTION

This invention relates in general to compositions for the treatment of *Clostridium difficile* associated diseases such as *Clostridium difficile* colitis, pseudomembranous colitis and antibiotic associated diarrhea and in particular to secretory immunoglobulin M (IgM) compositions administered in the form of pharmaceutical compositions.

BACKGROUND OF THE INVENTION

*Clostridium difficile* (*C. difficile*) is a gram-positive anaerobic *bacillus*.

Antibiotic associated pseudomembranous colitis results from the use of broad-spectrum antibiotic agents such as clindamycin. These antibiotics cause diarrhea in about 10% of treated patients and pseudomembranous colitis in about 1%. *C. difficile* causes antibiotic associated diarrhea and almost all cases of pseudomembranous colitis.

*Pseudomembranous colitis* results from the production of *C. difficile* toxin A (MW, 308,000) and toxin B (MW, 270,000) in the colon (Barroso et al., Nucleic Acids Res., 1990; 18:4004; Dove et al., Infect. Immun., 1990; 58:480-488; Lyerly et al., Clin. Microbiol. Rev., 1988; 1:1-18). Toxin A probably causes most of the gastrointestinal symptoms because of its enterotoxic activity (Lyerly et al., Infect. Immun., 1982; 35:1147-1150; Lyerly et al., Infect. Immun., 1985; 47:349-352). The toxins may act synergistically and the initial pathology caused by toxin A allows toxin B to manifest its toxicity (Lyerly et al., Infect. Immun., 1985; 47:349-352).

Most patients with *C. difficile* associated disease are treated effectively with vancomycin or metronidazole. Other treatment modalities include tolevemer, a toxin binding polymer (T. J. Louie et al., Clin. Infect. Dis. 2006; 43:411), and an antiparasitic medication, nitazoxanide (Med. Letter Drugs Ther. 2006; 48:89). However, relapses occur in about 20-25% of patients. Therefore, there is still a need for additional effective treatment of *Clostridium difficile* associated disease in humans.

Immunological treatment is valuable. Vaccination against toxins A and B stimulates active immunity against *C. difficile* disease in animals (Libby et al., Infect. Immun., 1982; 36:822-829). However, vaccines against the organism and its toxins are not available for human use.

Passive immunization is another immunological treatment. Serum antibodies against *C. difficile* protect hamsters against *C. difficile* disease after oral administration. Passive immunization with bovine antibodies has been proposed as a treatment for other infectious diseases of the gastrointestinal tract, such as diseases caused by rotavirus, enteropathogenic and enterotoxigenic *Escherichia coli*, *Vibrio cholerae*, and *Cryptosporidium parvum*. Preliminary studies indicate that such passive immunization provides protection (Boesman-Finkelstein et al., Infect. Immun., 1989; 57:1227-1234; Brussow et al., J. Clin. Microbiol., 1987; 25:982-986; Fayer et al., Infect. Immun., 1990; 58:2962-2965; Hilpert et al., J. Infect. Dis., 1987; 156:158-166; Mietens et al., Eur. J. Pediatr., 1979; 132:239-252; Tacket et al., N, Engl. J. Med., 1988; 318:1240-1243; Yoshiyama et al., Immunology, 1987; 61:543-547).

It has been reported that bovine immunoglobulin G (IgG) concentrate from the colostrum of cows vaccinated with *C. difficile* toxoid protects hamsters against antibiotic associated cecitis. The hamsters were protected when treated before the onset of diarrhea but not after diarrhea began (Lyerly et al., Infection and Immunity, Vol. 59, No. 6, pages 2215-2218 (1991)). IgG directed against toxins A and B of *C. difficile* are present in the general population (Bacon and Fekety, Diagn. Microbiol. Infect. Dis., 1994; 18:205-209). Human intravenous immunoglobulin derived from plasma donors has facilitated treatment in some patients, especially patients who lack circulating antibodies to the *C. difficile* toxins (Leung D. Y. et al., J. Pediatr. 1991 April; 118(4 (Pt 1)):633-7; Salcedo J. et al., Gut 1997; 41:366-370; Wilcox M. H., J. Antimicrob. Chemoth. 2004; 53:882-884; McPherson S. et al., Dis. Colon Rectum 2006; 49:640-645; Cone L. A. et al., Infect. Dis. Clin. Pract. 2006; 14:217-220).

In vitro experiments have demonstrated that polymeric immunoglobulin is superior to monomeric immunoglobulin in preventing *C. difficile* toxin damage to intestinal epithelial cell monolayers (Stubbe H. et al., J. Immunol. 2000; 164: 1952-1960).

Administration of an immunoglobulin product containing specific antibodies to *C. difficile* results in the elimination of *C. difficile* toxins and also killing of the bacteria within the colon as detailed in U.S. Pat. No. 5,773,000. Such passive immunization therefore provides an effective approach for the treatment of *C. difficile* associated diseases such as colitis, pseudomembranous colitis and antibiotic associated diarrhea. This is especially important for patients experiencing multiple relapses.

Current treatments for *C. difficile* associated disease use antibiotics such as metronidazole and vancomycin. These drugs result in further disruption of the intestinal flora and are associated with a 20-25% incidence of disease relapse.

Monomeric polyclonal IgA admixed with polyclonal IgG (2:1) was derived from plasma (IgAbulin, Immuno, Vienna) (100 mg/mL). Four mL was administered orally 3 times daily for 3 weeks to a three and one-half year old child with antibiotic-associated diarrhea and *C. difficile* toxin A in his stools. Vancomycin administration was continued concurrently. The child improved on this treatment (Tjellstrom B. et al., Lancet 1993; 341:701702). Polyclonal IgG derived from pooled plasma was administered to a second child with refractory *C. difficile* diarrhea who had failed treatment with antibiotics and intravenous polyclonal IgG. This patient received oral polyclonal IgG at 200 mg/kg/day every 2 days for 3 doses together with courses of oral vancomycin and *Lactobacillus*. The child had recovered at follow-up evaluation 2 weeks later (Saturna E J at al 2006). These reports demonstrate the efficacy of oral passive immunization with pooled immunoglobulins derived from the general population. It appears that monomeric circulatory immunoglobulins possess efficacy. However, increased efficacy is achieved by polymeric secretory IgM owing to the propensity of monomeric circulatory immunoglobulins to degrade in the gastrointestinal tract. The resultant dosing requirements increase treatment costs. The prior art use of circulatory immunoglobulins failed to explore secretory IgM as a potential medicament.

Thus, there exists a need for an IgM therapeutic that is resistant to gastrointestinal tract degradation. There also exists a need to provide such a therapeutic in a dosing form well suited for treating an infected subject.

SUMMARY OF THE INVENTION

A composition for treating a subject, especially a human subject, is provided. The composition includes a pentameric or hexameric IgM therapeutic that is formed by combining polyclonal pentameric or hexameric IgM containing J chain with a recombinant secretory component in a molar ratio of the pentameric or hexameric IgM to the secretory component of 1:1. Formulating agents are mixed with the pentameric or hexameric IgM to yield a dosing form of a capsule, tablet, and a suppository. The IgM therapeutic is optionally enterically coated or microencapsulated to withstand gastrointestinal exposure associated with oral delivery. The dosing form is in a daily amount of between 0.1 and 50 grams. The dosing form containing the IgM therapeutic optionally also includes an antibiotic.

A process for manufacturing a medicament for the treatment of C. difficile associated disease in a human is also provided that includes the collection of polyclonal pentameric or hexameric IgM as a byproduct of cold ethanol fractionation of pooled plasma derived from more than one human individual. The polyclonal pentameric or hexameric IgM is subjected to antiviral treatment to yield a virus free polyclonal pentameric or hexameric IgM that is also sterilized. The pentameric or hexameric IgM regardless of origin is modified with secretory component to form a secretory pentameric or hexameric IgM therapeutic. The pentameric secretory IgM therapeutic is then mixed with formulating agents to create a capsule, tablet, or suppository dosing form. The pooled plasma is optionally derived from specifically immune or immunized donors. The therapeutic is amenable to enrobement directly through microencapsulation or the dosing form is coated with an enteric coating. A method of treatment for C. difficile with the therapeutic is also provided. The treatment is amenable to supplementation with concurrent or prior antibiotic administration.

DETAILED DESCRIPTION OF THE PREFERRED EMBODIMENTS

The present invention has utility as a treatment for C. difficile infections. Unlike prior usage of monomeric IgA and IgG that is susceptible to gastrointestinal degradation, the present invention uses pentameric or hexameric secretory IgM. Because of its resistance to degradation in the gastrointestinal tract, it can be used at lower doses. Pentameric or hexameric IgM according to the present invention are bound to secretory component in order to mimic secretory IgA and IgM endogenous to the subject.

The present invention is superior to polymeric immunoglobulins administered orally because of the presence of secretory component protects the IgM from digestion in the gastrointestinal tract. Polyclonal immunoglobulins, including polyclonal pnetameric and hexameric IgM, directed against toxins A and B of C. difficile are present in the general population and are currently discarded as an unwanted byproduct of the manufacture of intravenous immunoglobulin. The present invention affords a prophylactic or active treatment of C. difficile disease alone, or in conjunction with a synergistic antibiotic. Current treatment of C. difficile associated disease is plagued by an unacceptable failure rate and antibiotic retreatment of patients with C. difficile associated disease results in the acquisition of additional unwanted antibiotic resistance.

As used herein, a "subject" is defined as a mammal and illustratively includes humans, non-human primates, horses, goats, cows, sheep, pigs, dogs, cats, and rodents.

As the present invention uses an immunoglobulin rather than antibiotics, an effective treatment is provided which does not disturb the intestinal flora.

The following description of the preferred embodiment(s) is merely exemplary in nature and is in no way intended to limit the invention, its application, or uses.

In one embodiment, the invention provides a method for medical treatment of humans involving the oral administration of a secretory IgM component which can be derived from a number of sources. One such source for the IgM is pooled human plasma following Cohn cold ethanol fractionation to produce fraction III precipitate as performed by those of skill in the art of protein separation. IgM byproduct is further purified by adsorption onto an ion exchange medium in neutral or slightly acidic conditions as performed by those of skill in the art of protein purification.

A more detailed description of isolation of an IgM component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may significantly selectively reduce the IgA and IgM concentrations. Such a step is important for producing immunoglobulin G for intravenous infusion into humans. This is because some individuals undergo an anaphylactic-like reactions if treated with intravenous IgG that contains IgA or IgM (which may activate complement) as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgM is generally discarded as an unwanted byproduct. According to the invention, this unwanted IgM following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the pentameric and hexameric IgM byproduct during the manufacture of intravenous immunoglobulin. From 5% to 10% of plasma IgM is pentameric and hexameric IgM (Carayannopoulos and Capra 1993). The resulting pentameric and hexameric IgM-J chains are purified.

In a preferred embodiment, the compositions of the invention contain, in addition to the IgM component, recombinant secretory component. Human secretory component can be produced by recombinant techniques as described in Crottet et al., Biochem. J. 1999; 341:299-306. The resulting pentameric and hexameric IgM is further coupled to recombinant secretory component as known to those skilled in the art (Bouvet J-P at al 1990; Prinsloo E at al 2006). Pentameric IgM containing both J chain and secretory component is again purified by ion-exchange and size exclusion chromatography and/or ultrafiltration as performed by those of skill in the art of protein purification. Purified pentameric and hexameric IgM containing secretory component is optionally stabilized for example by the addition of human serum albumin to a final concentration of 5%. The presence of the human J chains and secretory component in the compositions of the invention leads to doses of immunoglobulin M which are more physiologically effective than compositions without such components.

In another embodiment, a pentameric and hexameric IgM containing component is isolated as a byproduct from hyperimmune pooled human plasma for coupling with secretory component. Hyperimmune pooled human plasma is obtained from donors who have been immunized against a specific disease or are immune to the disease following natural infection. Pentameric and hexameric IgM contains 5, or 6, IgM monomers per J chain, respectively.

In another embodiment, the IgM composition contains a monoclonal antigen-specific IgM (United States Patent Application 20070154469 Irie; Reiko Jul. 5, 2007); the IgM component is further combined with recombinant secretory component to produce a more physiologically effective composition.

The secretory IgM antibodies may be administered alone as a liquid or solid, preferably in a solid powder form and preferably in admixture with a carrier to form a pharmaceutical composition such as a tablet, capsule or suppository.

Since preferred methods of administration are oral and rectal, or enteric installation, and most preferred is oral, with solid oral dosage forms such as tablets and capsules being especially preferred, or enteric installation. These are prepared according to conventional methods known those skilled in the art. The secretory IgM antibodies may also be combined with other pharmaceutically acceptable carriers such as various liquids, proteins or oils which may also provide additional nutritional and/or pharmaceutical benefits. Remington Science and Practice of Pharmacy, 20$^{th}$ ed. (2000).

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385,078; 4,518, 433; and 4,556,552.

They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore melt in the rectum or vaginal cavity and release the active component.

Since the effect of the secretory IgM antibody is dependent on its reaching the colon, preferred tablets or capsules are enteric coated. Alternatively, the active secretory IgM antibodies can themselves be microencapsulated prior to formulation. Preparation of microcapsules of secretory IgM antibody as well as preparation of enteric coated tablets or capsules can be achieved by conventional methods as detailed above.

Because the secretory IgM antibodies first eliminate the *C. difficile* toxins, it is also advantageous to administer to patients suffering from *C. difficile* associated diseases a combination of the secretory IgM antibodies of the present invention with antibiotics that are known for treating pseudomembranous colitis and/or antibiotic associated diarrhea. Such antibiotics are for example vancomycin, and metronidazole. Because of the prompt elimination of the *C. difficile* toxins, the combination of secretory IgM antibody and antibiotic may be synergistic requiring a shorter duration of antibiotic treatment with decreased symptoms, faster symptomatic relief and a lower relapse rate. Recognized doses for administering metronidazole for example is 250 mg four times a day, and oral vancomycin is 125 mg four times a day. Administration of these antibiotics with the secretory IgM antibody of the present invention would result in use of substantially reduced dosage of antibiotics.

The administration of such combination antibiotic and secretory IgM treatment may be in a single dosage form where both active ingredients are combined and mixed with a pharmaceutically acceptable carrier. Preferred compositions would be those adapted for oral or rectal administration and it would include solid oral dosing forms such as enteric coated tablets or capsules, or suppositories.

The administration of the combination concurrently or following one another in separate dosage forms may still be formulated together in divided tablets or capsules. These are also known to those skilled in the pharmaceutical art.

Treatment of patients suffering from *C. difficile* associated diseases with the combination of two active ingredients can take place not only concurrently in a single or separate dosage form but also following administration of one ingredient with the other. Preferably, administration of the inventive IgM is followed by administration of the antibiotic.

The antibody of the present invention is contained in secretory IgM provided to a subject suffering *C. difficile* infection or symptoms thereof. In such form, the amount of secretory IgM provided to the patient is about 1 gram per day. Typically amounts from about 0.1 to 50 grams per day will be used and preferably, 1 to 10 grams per day. For example, about 1 to 2 grams of secretory IgM could be given to a subject 3 to 4 times per day. The doses of the secretory IgM antibody formulation to be administered will depend upon the subject and the subject's medical history. Dosages of the specific secretory IgM for adult humans envisioned by the present invention and considered to be therapeutically effective will range from between about 0.1 to 500 mg. However, it is to be understood that doses can readily be adjusted to provide appropriate amounts of the secretory IgM antibody to any subject, including children.

Diseases and conditions for which administration of the compositions of the invention is to be used therapeutically or prophylactically include, but are not limited to: common variable immunodeficiency, IgA deficiency, human immunodeficiency virus (HIV) infection, bacterial and viral infections such as lower respiratory tract infection with influenza, lower respiratory tract infection with respiratory syncytial virus, lower respiratory tract infection with rhinovirus, lower respiratory tract infection with adenovirus: protozoan infections such as giadiasis, yeast infections; chronic lymphocytic leukemia; multiple myeloma; macroglobulinemia; chronic bronchitis; bronchiectasis; asthma; immune suppression associated with bone marrow transplantation; immune suppression associated with cyclophosphamide administration; immune suppression associated with azathiaprine administration; immune suppression associated with methotrexate administration; immune suppression associated with chlorambucil administration; immune suppression associated with nitrogen mustard administration; immune suppression associated with 6-mercaptopurine administration; immune suppression associated with thioguanine administration; severe combined immunodeficiency; adenosine deaminase deficiency; major histocompatibility class I (Bare leukocyte syndrome) and class II deficiencies; purine nucleoside phosphorylase deficiency; DiGeorge Syndrome; transient hypogammaglobulinemia of infancy; X-linked agammaglobulinemia; X-linked agammaglobulinemia with growth hormone deficiency; transcobalamin II deficiency; immunodeficiency with thymoma; immunodeficiency with hereditary defective response to Epstein Barr virus; immunoglobulin deficiency with increased IgM; P chain deficiency; ataxia telangiectasia; immunodeficiency with partial albinism; sequelae of selective IgA deficiency such as those due to rheumatoid arthritis; juvenile rheumatoid arthritis; systemic lupus erythematosus; thyroiditis; pernicious anemia; dermatomyositis; Coomb's positive hemolytic anemia; idiopathic Addison's disease; cerebral vasculitis and idiopathic thrombocytopenic purpura.

The invention is further described by reference to the following detailed examples, wherein the methodologies are as described below. These examples are not meant to limit the scope of the invention that has been set forth in the foregoing description. Variations within the concepts of the invention are apparent to those skilled in the art.

Example 1

Polyclonal IgM is obtained from pooled human plasma following Cohn cold ethanol fractionation to produce fraction III precipitate. IgM is further purified by adsorption onto an ion exchange medium in neutral or slightly acidic conditions. IgM-J chain pentamers and hexamers are purified. IgM-J chain pentamers and hexamers are then further coupled to recombinant secretory component again by disulfide bonding in mildly oxidizing conditions, preferably at a molar ratio of secretory component to IGM-J chain pentamers and hexamer of 1:1. IgM containing both J chain and secretory component is again purified. Purified IgM containing J chain and secretory component is stabilized by the addition of human serum albumin to a final concentration of 5%. The final solution is adjusted to a therapeutic dose of 5 mg IgM.

An ELISA assay will be used to confirm that the IgM preparation contains specific anti-*C. difficile* IgM.

ELISA Method

Human secretory IgM levels to *C. difficile* is measured by ELISA using a modification of the method previously described (C. P. Kelly et al., Gastroenterology 1992; 102: 3540; D. Y. M. Leung et al., J. Pediatr. 1991; 118:633-637 and Bacon and Fekety. Diagn. Microbiol. Infect. Dis. 1994; 18:205-209). Coating antigens used to measure IgM titers included purified *C. difficile* toxin A and purified *C. difficile* toxin.

Toxigenic *Clostridium difficile* is cultured for 72 hours in brain heart infusion broth (Beckton Dickinson, Cockeysville, Md.). The conditioned medium is centrifuged and the supernatant filter sterilized by passage through a 45 um filter (Nalgene). *C. difficile* toxins A and B are purified from the broth culture supernatant as previously described (C. Pothoulakis et al., J. Clin. Invest. 1991; 88:119-125).

Microtiter plates (Immulon II, Dynatech) are coated with C. difficile toxin A or toxin B (each at 10 μg protein per ml in carbonate buffer pH 9.6, 100 μl per well) by incubation for 2 hours at 37° C. followed by overnight incubation at 4° C. Plates are washed between each incubation step using phosphate buffered saline with 0.05% Tween 20 (PBS-T). Plates are then blocked with 2% human serum albumin (ICN, 100 μl/well) in PBS and incubated for 1 hour at room temperature.

All assays are performed in triplicate.

Horseradish peroxidase-labeled goat anti-human IgM (catalog number STAR98P, AbD Serotec) is used as the secondary antibody (0.2 ug/ml in PBS with 2% human serum albumin) incubated for one hour at 37° C. TMB microwell peroxidase substrate (KPL Laboratories) is used as substrate (100 μl/well) and stopped after 2 to 5 minutes with an equal volume of 1 M phosphoric acid. The optical density is then read at 450 nm with 630 nm as reference using an automated photometer (Dynatech). Controls include substitution of the secondary antibody with peroxidase labeled anti-murine IgM and omission of the peroxidase substrate solution. Results are expressed at the mean optical density of test wells minus mean optical density of background wells (coated with human serum albumin alone).

Example 2

To demonstrate that secretory IgM is capable of inhibiting the enterotoxic effects of C. difficile toxins.

Enterotoxicity Method

Fasting male Wistar rats are anesthetized by intraperitoneal injection of sodium pentobarbital. Laparotomy is performed, the renal pedicles tied and 3H-mannitol (10 μCi, PerkinElmer Life Sciences, Boston, Mass.) administered intravenously. Closed ileal loops (5 cm) are then formed and injected with 400 μl of 50 mM Tris buffer (pH 7.4) or with Tris buffer containing C. difficile culture filtrate (20 ug of protein). The inhibitory effect of secretory IgM is assessed by the addition of secretory IgM (200 ug) to the toxins prior to injection into the ileal lumen.

The abdominal incision is closed and anesthesia maintained with sodium pentobarbital. The animals are sacrificed after 4 hours and the ileal loops immediately harvested. Loop weight to length ratio is determined as a measure of enterotoxin effect. Mannitol excretion, indicating intestinal permeability, is measured by counting radioactivity in the luminal fluid. Ileal tissue samples are also fixed in formalin, paraffin-embedded and sections stained with hematoxylin and eosin. The histologic severity of enteritis is graded taking into account the following features: i) neutrophil margination and tissue infiltration, ii) hemorrhagic congestion and edema of the mucosa, iii) epithelial cell damage. A score of 0 to 3 denotes increasingly severe pathological changes.

Example 3

Treatment of a Person Ill with *C. difficile* Associated Disease with Secretory IgM An adult individual ill with *C. difficile* associated disease is treated with secretory IgM containing antibody activity against *C. difficile* toxin. Treatment is with 1 gram orally three times daily together with vancomycin in appropriate dosage. Treatment is continued until symptoms resolve and the stool becomes negative for *C. difficile* toxin.

REFERENCES

Bacon A. E. 3rd, Fekety R. Immunoglobulin G directed against toxins A and B of *Clostridium difficile* in the general population and patients with antibiotic-associated diarrhea. Diagn. Microbiol. Infect. Dis. 1994; 18:205-209.

Barroso L. A., Wang S. Z., Phelps C. J., Johnson J. L., Wilkins T. D. Nucleotide sequence of *Clostridium difficile* toxin B gene. Nucleic Acids Res. 1990; 18:4004.

Berzofsky J. A., Berkower I. J., Epstein S. L., Monoclonal Antibodies in Chapter 12, Antigen-Antibody Interactions and Monoclonal Antibodies, pp. 455-465 in Fundamental Immunology, Third Edition, W. E. Paul (ed), Raven Press, NY 1993.

Boesman-Finkelstein M., Walton N. E., Finkelstein R. A. Bovine lactogenic immunity against cholera toxin-related enterotoxins and *Vibrio cholerae* outer membranes. Infect. Immun. 1989; 57:1227-1234.

Bouvet J P, Pillot J, Iscaki S. Secretory component-binding properties of normal serum IgM. Scand J Immunol. 1990; 31:437-441.

Brussow H., Hilpert H., Walther I., Sidoti J., Mietens C., Bachmann P. Bovine milk immunoglobulins for passive immunity to infantile rotavirus gastroenteritis. J. Clin. Microbiol. 1987; 25:982-986.

Carayannopoulos L., Capra J. D. Chapter 9 Immunoglobulins Structure and Function pp. 283-314 in Fundamental Immunology, Third Edition, W. E. Paul (ed), Raven Press, NY 1993.

Cohn E. J., Strong L. E., Hughes W. L., Jr., Mulford D. J., Ashworth J. N., Melin M., Taylor H. L., Preparation and Properties of Serum and Plasma Proteins IV. A System for the Separation into Fractions of the Protein and Lipoprotein Components of Biological Tissues and Fluids, J. Am. Chem. Soc. 1946; 68; 459-475.

Cone L. A., Lopez C., Tarleton H. L., Jodoin D., Taylor M., Gade-Andavolu R., Dreisbach L. P. A durable response to relapsing *Clostridium difficile* colitis may require combined therapy with high-dose oral vancomycin and intravenous immune globulin. Infect. Dis. Clin. Pract. 2006; 14:217-220.

Corthesy B., Recombinant Secretory IgA for Immune Intervention Against Mucosal Pathogens, Biochem. Soc. Trans. 1997, 25; 471-475.

Corthier et al., Emergence in Gnotobiotic Mice of Nontoxinogenic Clones of *clostridium dificile* from a Toxinogenic One, Infection and Immunity, Jun. 1988, pp. 1500-1504.

Corthier et al., Protection Against Experimental Pseudomembranous Colitis in Gnotobiotic Mice by Use of Monoclonal Antibodies Against *clostridium difficile* Toxin A, Infection and Immunity, March 1991, pp. 1192-1195.

Crottet P., Cottet S., Corthesy B., Expression, Purification and Biochemical Characterization of Recombinant Murine Secretory Component, A Novel Tool in Mucosal Immunology, Biochem. J. 1999, 341; 299-306.

Dove C. H., Wang S. Z., Price S. B., Phelps C. J., Lyerly D. M., Wilkins T. D. and Johnson J. L.; Lyerly et al. Molecular characterization of the *Clostridium difficile* toxin A gene. Infect. Immun. 1990; 58:480-488.

Ehrich et al., Production of *clostridium difficile* Antitoxin, Infection and Immunity, June, 1980, pp. 1041-1043.

Fayer R., Guidry A., Blagburn B. L. Immunotherapeutic efficacy of bovine colostral immunoglobulins from a hyperimmunized cow against cryptosporidiosis in neonatal mice. Infect. Immun., 1990; 58:2962-2965.

Gerding et al., *clostridium difficile*-Associated Diarrhea Archives of Internal Medicine, vol. 146, January 1986, pp. 95-100.

Hilpert H., Brussow H., Mietens C., Sidoti J., Lerner L., Werchau H. Use of bovine milk concentrate containing antibody to rotavirus to treat rotavirus gastroenteritis in infants. J. Infect. Dis. 1987; 156:158-166.

Kelly et al., *clostridium difficile* Colitis, New England Journal of Medicine, vol. 330, January 1994, pp. 257-262.

Kelly et al., Human Colonic Aspirates Containing Immunoglobulin A Antibody to *clostridium difficile* Toxin A Inhibit Toxin A-Receptor Binding, Gastroenterology, vol. 102, No. 1, pp. 35-40.

Kohler G., Milstein C., Continuous Cultures of Fused Cells Secreting Antibody of Predetermined Specificity, Nature 1975; 256; 495-497.

Leung D. Y., Kelly C. P., Boguniewicz M., Pothoulakis C., LaMont J. T., Flores A. Treatment with intravenously administered gamma globulin of chronic relapsing colitis induced by *Clostridium difficile* toxin. J. Pediatr. 1991 April; 118(4 (Pt 1)):633-637.

Libby J. M., Jortner B. S., Wilkins T. D. Effects of the two toxins of *Clostridium difficile* in antibiotic-associated cecitis in hamsters. Infect. Immun. 1982 May; 36(2):822-829.

Lima et al., Effects of *clostidium difficile* Toxins A and B in Rabbit Small and Large Intestine In Vivo and on Cultured Cells In Vitro, Infection and Immunity, March 1988, pp. 582-588.

Louie T. J., Peppe J., Watt C. K., Johnson D., Mohammed R., Dow G., Weiss K., Simon S., John J. F. Jr., Garber G., Chasan-Taber S., Davidson D. M.; Tolevamer Study Investigator Group. Tolevamer, a novel nonantibiotic polymer, compared with vancomycin in the treatment of mild to moderately severe *Clostridium difficile*-associated diarrhea. Clin. Infect. Dis. 2006; 43:411-20.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Lyerly D. M., Krivan H. C., Wilkins T. D. *Clostridium difficile*: its disease and toxins. Clin. Microbiol. Rev. 1988; 1:1-18.

Lyerly D. M., Phelps C. J., Toth J., Wilkins T. D. Characterization of toxins A and B of *Clostridium difficile* with monoclonal antibodies. Infect. Immun. 1986; 54:70-76.

Lyerly D. M., Bostwick E. F., Binion S. B., Wilkins T. D. Passive immunization of hamsters against disease caused by *Clostridium difficile* by use of bovine immunoglobulin G concentrate. Infect. Immun. 1991; 59:2215-2218.

Lyerly D. M., Lockwood D. E., Richardson S. H., Wilkins T. D. Biological activities of toxins A and B of *Clostridium difficile*. Infect. Immun. 1982; 35:1147-1150.

Lyerly D. M., Saum K. E., MacDonald D. K., Wilkins T. D. Effects of *Clostridium difficile* toxins given intragastrically to animals. Infect. Immun. 1985; 47:349-352.

Mahe et al., Effect of Various Diets on Toxin Production by Two Strains of *clostridium difficile* in Gnotobiotic Mice, Infection and Immunity, August 1987, pp. 1801-1805.

Martinez et al., Purification and Characterization of *clostridium sordellii* Hemorrhagic Toxin and Cross-Reactivity with *clostridium difficile* Toxin A (Enterotoxin), Infection and Immunity, May 1988, pp. 12-15-1221.

McFarland et al., Nosocomial Acquisition of *clostridium difficile* Infection, The New England Journal of Medicine, January 1989, pp. 204-210.

McFarland et al., Review of *clostridium difficile* Associated Diseases, American Journal of Infection Control, vol. 14, No. 3, June 1986, pp. 99-104.

McPherson S., Rees C. J., Ellis R., Soo S, and Panter S. J. Intravenous Immunoglobulin for the Treatment of Severe, Refractory, and Recurrent *Clostridium difficile* Diarrhea. Diseases of the Colon & Rectum. 2006; 49(5):640-645.

Med. Letter Drugs Ther. 2006; 48:89-90, 92.

Mietens C., Keinhorst H., Hilpert H., Gerber H., Amster H., Pahud J. J. Treatment of infantile *E. coli* gastroenteritis with specific bovine anti-*E. coli* milk immunoglobulins. Eur. J. Pediatr. 1979; 132:239-252.

Mitchell et al., Effect of Toxin A and B of *clostridium difficile* on Rabbit Ileum and Colon, Gut, 1986, vol. 27, pp. 78-85.

Morris et al., Role of Surgery in Antibiotic-Induced Pseudomembranous Enterocolitis, The American Journal of Surgery, vol. 160, November 1990, pp. 535-539.

Oncley J. L., Melin M., Richert D. A., Cameron J. W., Gross P. M., Jr., The Separation of the Antibodies, Isoagglutinins, Prothrombin, Plasminogen and β1-Lipoprotein into Subfractions of Human Plasma. J. Am. Chem. Soc. 1949; 71:541-550.

Pothoulakis C., LaMont J. T., Eglow R., Gao N., Rubins J. B., Theoharides T. C., Dickey B. F. Characterization of rabbit ileal receptors for *Clostridium difficile* toxin A. Evidence for a receptor-coupled G protein. J. Clin Invest. 1991; 88:119-25.

Prinsloo E, Oosthuizen V, Muranmoto K, Naude R J. In vitro refolding of recombinant human free secretory component using equilibrium gradient dialysis. *Protein Expr Purif.* 2006; 47:179-185.

Rothman et al., Differential Cytotoxic Effects of Toxins A and B Isolated from *clostridium difficile*, Infection and Immunity, November 1984, pp. 324-331.

Salcedo J. et. al. Gut 1997; 41:366-370.

Saturno E. J., Costa H., Sorensen R. Oral Immunoglobulin Therapy in a Child with Severe *Clostridium Difficile* Diarrhea. J Allergy Clin Immunol 2006; 117:S284.

Strong L. E., Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, NY 1963, pp. 576-602.

Stubbe H. et al. J. Immunol. 2000; 164:1952-1960.

Symersky J., Novak J., McPherson D. T., DeLucas L., Mestecky J. Expression of the recombinant human immunoglobulin J chain in *Escherichia coli*. Mol. Immunol. 2000; 37:133-140.

Tacket C. O., Losonsky G., Link H., Hoang Y., Guesry P., Hilpert H., Levine M. M. Protection by milk immunoglobulin concentrate against oral challenge with enterotoxigenic *Escherichia coli*. N. Engl. J. Med. 1988; 318:1240-3.

Tjellstrom B., Stenhammar L., Eriksson S., Magnusson K. E. Oral immunoglobulin A supplement in treatment of *Clostridium difficile* enteritis. Lancet 1993; 341(8846):701-702.

Triadafilopoulos et al., Differential Effects of *clostridium difficile* Toxins A and B on Rabbit Ileum, Gastroenterology, 1987, vol. 93, pp. 273-279.

Tucker et al., Toxin A of *clostridium difficile* Is a Potent Cytotoxin, Journal of Clinical Microbiology, May 1990, pp. 869-871.

Weltzin R., Traina-Dorge V., Soike K., Zhang J. Y., Mack P., Soman G., Drabik G., Monath T. P., Intranasal Monoclonal IgA Antibody against Respiratory Syncytial Virus Protects Rhesus Monkeys against Upper and Lower Respiratory Tract Infection. J. Infect. Dis. 1996; 174:256-261.

Weltzin R., Hsu S. A., Mittler E. S., Georgakopoulas K., Monath T. P., Intranasal Monoclonal Immunoglobulin A against Respiratory Synctial Virus Protects against Upper and Lower Respiratory Tract Infections in Mice. Antimicrob. Agents Chemother. 1994; 38:2785-2791.

Wilcox M. H. J. Antimicrob. Chemoth. 2004; 53:882-884.

Yoshiyama Y., Brown W. R. Specific antibodies to cholera toxin in rabbit milk are protective against *Vibrio cholerae-induced* intestinal secretion. Immunology. 1987; 61:543-547.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following clams, including all equivalents thereof, are intended to define the scope of the invention.

The invention claimed is:

1. A composition comprising polyclonal IgM-J chain pentamers obtained from plasma;
    the polyclonal IgM-J chain pentamers combined with a recombinant secretory component in a molar ratio of the IgM-J chain pentamers to the secretory component of 1:1 forming a secretory pentameric IgM.

2. The composition of claim 1 wherein the IgM-J chain pentamers are combined with said recombinant secretory component by a disulfide linkage.

3. The composition according to claim 1, wherein the plasma is obtained from specifically immune or immunized donors.

4. The composition of claim 1 further comprising excipients to form a tablet or a capsule.

5. The composition of claim 1, further comprising a inicroencapsulant encompassing said secretory pentameric IgM.

6. The composition of claim 4 further comprising at least one antibiotic present in said tablet or capsule.

7. The composition of claim 6 wherein said antibiotic is at least one of vancomycin and metronidazole.

8. A process for treating *C. difficile* associated disease in a human comprising:
    administering to said human suffering therefrom a therapeutically effective amount of a composition comprising polyclonal IgM-J chain pentamers obtained from plasma, the polyclonal IgM-J chain pentamers combined with a recombinant secretory component in a molar ratio of the IgM-J chain pentamers to the secretory component of 1:1 forming a secretory pentameric IgM, wherein the composition binds to a toxin produced by *C. difficile*.

9. The process of claim 8 further comprising combining an excipient with the composition to yield a dosing form selected from the group consisting of: a solid oral dosing form, a liquid oral dosing form, and a suppository.

10. The process of claim 8 wherein the therapeutically effective amount is between 0.1 and 50 grams daily.

11. The process of claim 8 further comprising administering an antibiotic with or prior to said the composition.

12. The process of claim 11 wherein the antibiotic is administered and discontinued prior to the administration of the composition.

13. A process for manufacturing a medicament for the treatment of *C. difficile* associated disease in a human comprising:
    collecting polyclonal pentameric IgM containing J chain as a byproduct of cold ethanol fractionation or of ion exchange chromatographic fractionation of pooled plasma obtained from more than one human individual;
    subjecting the polyclonal pentameric IgM containing J chain to antiviral treatment to yield a virus free polyclonal pentameric IgM;
    sterilizing the virus free polyclonal pentameric IgM containing J chain to yield sterile polyclonal pentameric IgM;
    modifying the sterile polyclonal pentameric IgM with secretory component to form secretory pentameric IgM; and
    mixing the pentameric secretory IgM with an excipient to yield a dosing form selected from the group consisting of: solid oral, liquid oral, and a suppository;
    wherein said pentameric IgM binds to a toxin produced by *C. difficile*.

14. The process of claim 13 further comprising adding an enteric coating to the dosing form.

15. The process of claim 13 further comprising microencapsulating the pentameric secretory IgM.

16. The process of claim 13, wherein the pooled plasma is obtained from specifically immune or immunized donors.

17. The method of claim 14 further comprising:
    providing the human with an amount of an antibiotic selected from the group consisting of: vancomycin and metronidazole.

18. A composition comprising IgM and a recombinant J chain and further comprising a recombinant secretory component.

19. The composition of claim 18 wherein the IgM is human IgM.

20. The composition of claim 18 wherein the IgM is monoclonal IgM.

21. The composition of claim 18 wherein the secretory component is a human secretory component.

* * * * *